United States Patent [19]
Ho et al.

[11] Patent Number: 5,466,443
[45] Date of Patent: Nov. 14, 1995

[54] HERBAL-BASED ORAL COMPOSITION AND PROCESS FOR PRODUCING THE SAME

[75] Inventors: Shu K. Ho, No. 3, Kam Lam St., Kwong Fung Building, 13th Floor, Flat K, Mongkok, Kowloon, Hong Kong; Yi F. Yao, Shijiazhuang, China

[73] Assignee: Shu K. Ho, Kowloon, Hong Kong

[21] Appl. No.: 252,101

[22] Filed: May 31, 1994

[51] Int. Cl.$^6$ ................ A61K 7/06; A61K 35/78
[52] U.S. Cl. .............. 424/70.6; 424/74; 424/195.1
[58] Field of Search .............. 424/195.1, 70.6, 424/70.1, 74, 401, 435, 485, 58; 514/944, 880, 783

[56] References Cited

U.S. PATENT DOCUMENTS

| | | | |
|---|---|---|---|
| 4,817,640 | 4/1989 | Summers | 131/359 |
| 5,376,374 | 12/1994 | Zelaya | 424/195.1 |

FOREIGN PATENT DOCUMENTS

| | | |
|---|---|---|
| 89102379.8 | 4/1989 | China. |

OTHER PUBLICATIONS

Zviak, *The Science of Hair Care*, 1986, pp. 447–450.
Maoshing Ni, C. A., *Chinese Herbology Made Easy*, pp. 138–140 and 148–151, 182, 183.
Translated and Chinese Language Excerpt from *Encyclopedia of Chinese Medicine and Herbs*.

*Primary Examiner*—Thurman K. Page
*Assistant Examiner*—Sally Gardner
*Attorney, Agent, or Firm*—Christensen, O'Connor, Johnson & Kindness

[57] ABSTRACT

An herbal-based oral composition for promoting darkening of human hair color upon periodic retention of the composition within the oral cavity includes an herbal mixture included at a level of from 2.5 to 15% of the total weight of the herbal mixture in a toothpaste or chewing gum base. The herbal mixture includes prepared *Rhizoma Ligustici Chuanxiong, Calculus Bovis, Indigo Naturalis, Herba Ecliptae, Radix Polygoni Multiflori, Pericarpium Trichosanthis, Radix Sophorae Flavescentis, Spina Gleditsiae, Radix Angelicae Sinensis, Rhizoma Drynariae, Fructus Mori,* and Halitum. The composition is found effective at darkening hair color when held in the oral cavity for a short period of time two times a day for a period of six weeks.

3 Claims, No Drawings

HERBAL-BASED ORAL COMPOSITION AND PROCESS FOR PRODUCING THE SAME

FIELD OF THE INVENTION

The present invention relates to herbal-based products, in particular to herbal-based gums and toothpastes for promoting darkening of hair color.

BACKGROUND OF THE INVENTION

Chinese herbalists have over the centuries identified individual herbs that are believed to have certain beneficial effects on the human body. Included among these herbs are *Radix Polygoni Multiflori*, referred to by Chinese herbalists as He Shou Wu. This herb is traditionally believed to be useful in the treatment of kidney and liver deficiencies, premature graying of the hair, relief of constipation, and skin lesions. Another traditional herb is *Rhizoma Drynariae*, otherwise known as Gu Sui Bu, which is traditionally believed to aid the liver and kidney, to assist in the healing of bone fractures, dislocations and tissue trauma, and to reduce premature balding and to promote hair growth. The physical characteristics of these herbs and their methods of preparation are described in the *Encyclopedia of Chinese Medicine and Herbs*, which disclosure is hereby expressly incorporated by reference. A traditional generalization of the operation of these herbs the symptomology for which they are useful, and the activity are described in Ni, Maoshing, *Chinese Herbology Made Easy*, pages 138–140, 148, 149, 150, and 151, the disclosure of which is hereby expressly incorporated by reference. A still further traditional Chinese herb is *Herba Ecliptae*, which has traditionally been believed to aid in restoring grayed hair to its original color, and to lessen the loss of hair.

These individual herbs are traditionally administered by ingesting, i.e., swallowing, the herbs. However, it has been found that the activity of these herbs is greatly reduced because the herbs are destroyed by stomach acids before they have had an opportunity to be absorbed into the blood stream.

SUMMARY OF THE INVENTION

The present invention provides a composition including traditional Chinese herbs that have been compounded to produce a composition that the inventors have found to promote the darkening and regrowth of human hair. This composition is delivered in an oral retention base so that extracts of the herbs enter the bloodstream through buccal absorption, which greatly increases the effectiveness of the herbs.

The herbal-based oral composition of the present invention is intended for periodic retention within the oral cavity of a human, and includes herbs selected from the group consisting of *Radix Polygoni Multiflori, Rhizoma Drynariae, Herba Ecliptae*, and mixtures thereof. These herbs are compounded in a viscous oral retention base.

In a preferred embodiment, the herbal composition also includes *Rhizoma Ligustici Chuanxiong, Calculus Bovis, Indigo Naturalis, Pericarpium Trichosanthis, Radix Sophorae Flavescentis, Spina Gleditsiae, Radix Angelicae Sinensis, Fructus Mori*, and Halitum. The viscous oral retention base is selected from the group consisting of gums, gels, and pastes, and thus may be administered in the form of a toothpaste or a chewing gum.

An additional aspect of the invention provides a method of delivering an herbal product that promotes darkening of human hair color upon periodic retention of the composition within the oral cavity, comprising administering an effective amount of herbs selected from the group consisting of *Radix Polygoni Multiflori, Rhizoma Drynariae, Herba Ecliptae*, and mixtures thereof in an oral retention base to the oral cavity of a human for buccal absorption of extracts of the herbs.

In a further aspect of the present invention, a process for producing the herbal-based composition is provided, which comprises compounding an effective amount of the herbs with an oral retention base.

DETAILED DESCRIPTION OF THE PREFERRED EMBODIMENT

The present invention provides an herbal-based composition consisting of an herbal mixture compounded into a viscous oral retention medium. The herbal ingredients are selected and prepared to provide a composition that is effective at causing human scalp and facial hair to darken, to reduce loss of scalp hair, and to promote hair growth after a period of repeated usage. The critical ingredients in this herbal composition are *Radix Polygoni Multiflori and Rhizoma Drynariae*. While either of this is believed to have some effectiveness when used alone, the effectiveness is greatly enhanced when both are used in combination, and is further enhanced when combined with Herba Ecliptae. The effectiveness is still further enhanced when these herbs are combined with the following additional herbs and ingredients: *Rhizoma Ligustici Chuanxiong, Calculus Bovis, Indigo Naturalis, Pericarpium Trichosanthis, Radix Sophorae Flavescentis, Spina Gleditsiae, Radix Angelicae Sinensis, Fructus Mori*, and Halitum. Trace amounts of residue from black beans, Chinese white vinegar, Chinese rice wine, and a small quantity of cane sugar, which are used in processing the herbs are also included. Water is also included to place the herbs, each of which is prepared in a powdered form, into an aqueous suspension. This suspension is then compounded with a viscous base, such as a toothpaste, oral gel, or chewing gum base.

The preferred formulation of the herbal composition of the present invention is provided in Table 1 below. These ingredients are combined in the quantities listed in accordance with the procedure that will be set forth below, to yield a total aqueous suspension of the herbal mixture of approximately 18 kg. This approximate 18 kg. of the herbal mixture is then compounded with the oral retention base to yield approximately 2000 to 2400 tubes of toothpaste, each tube weighing approximately grams (2.26 oz.), or approximately 300,000 sticks of chewing gum.

For the toothpaste, approximately 18 kg. of herbal mixture is compounded with sufficient toothpaste base to yield 128 to 154 kg. of herbal toothpaste. Thus the herbal mixture is included at a level of from approximately 11.7 to 14% by weight of the total herbal mixture-plus-toothpaste base composition. The *Radix Polygoni Multiflori* is included at a level of from 3.8 to 4.5% by weight of the total toothpaste composition, the *Rhizoma Drynariae* is included at a level of from 2.6 to 3.1% by weight of the total toothpaste composition and the *Herba Ecliptae* is included at a level of from 1.4 to 1.7% by weight of the total toothpaste composition. The weight ratio of Radix Polygoni Multiflori to Rhizoma Drynariae is approximately 1.5:1.

TABLE I

Herbal Mix - Active Ingredients

| Quantity (grams) | Ingredient |
| --- | --- |
| 24.6 | *Rhizoma Ligustici Chuanxiong* |
| 2.3 | *Calculus Bovis* |
| 983.0 | *Indigo Naturalis* |
| 2150.0 | *Herba Ecliptae* |
| 5820.0 | *Radix Polygoni Multiflori* |
| 480.0 | *Pericarpium Trichosanthis* |
| 1970.0 | *Radix Sophorae Flavescentis* |
| 2,075.0 | *Spina Gleditsiae* |
| 500.0 | *Radix Angelicas Sinensis* |
| 3,960.0 | *Rhizoma Drynariae* |
| 15.4 | *Fructus Mori* |
| Trace | Black bean |
| Trace | Chinese white vinegar |
| Trace | Chinese rice wine |
| Trace | Cane sugar |
| 20.0 | Halitum |
| ~20.0 | Water |
| 18,020 grams | |

In order to enhance the traditional medicinal benefits of these herbs, it is also preferable to compound the following additional herbs with those listed above in the toothpaste or gum composition: *Radix Ginseng, Cornu Cervi Pantot, Spica Prunellae, Herba Andrographitis, Flos Chrysanthemi Indici, Herba Houttuyniae,* and *Retinervus Luffae Fructus.*

When the herbal extract has been compounded with the oral retention base, such as a toothpaste, oral gel, or chewing gum, it is retained within the user's mouth for a sufficient period of time to enable extract, i.e. the active, ingredients, of the herbs to be absorbed through the mouth tissue in the buccal cavity. For example, the composition can be formulated as a toothpaste for oral delivery of the herbs by buccal absorption. When used in this way, the paste is applied on a toothbrush and worked to a foam in the user's mouth, as with conventional toothpaste. This foam paste is carried in the user's mouth for approximately five minutes. While some users report swallowing the paste, it is recommended that the paste be spit out rather than ingested at this point. Brushing with the paste and retention for five minutes each time is repeated twice a day. Beneficial effects of the paste are evidenced after six weeks of continuous use in this fashion, with the benefit increasing over a total of five months of use.

Testing of the toothpaste composition of the present invention in the People's Republic of China, at the Beijing Red Cross Chaouang Hospital and the Juanganmen Hospital—Research Institute of Traditional Chinese Medicine found the composition to be 79% effective at causing visible darkening of scalp and facial hair to its original color, i.e., gray hair is returned to its original black, brunette, or blond coloring. Thickening and regrowth of the hair has also been reported. It is advised that during the five-month treatment period, eating of raw onion, garlic, or radish be avoided. Other benefits of the herbs that have traditionally been detected, as disclosed in the *Encyclopedia of Chinese Medicine* and Herbs and Ni, Maoshing, *Chinese Herbology Made Easy,* are also believed to result by application of the composition of the present invention by the oral retention method of delivery disclosed herein.

The process for preparing the aqueous suspension of the herbal mixture toothpaste composition of the present invention shall now be described. A first herbal mixture is prepared as follows: 10 kg. of black beans are boiled in 40 kg. of water until the liquid volume is reduced to 20 kg. The beans are discarded, and 10 kg. of dry *Radix Polygoni Multiflori* are added to the liquid. The liquid is then boiled for at least four hours until all of the visible water is removed. The resulting *Radix Polygoni Multiflori* is then thoroughly air-dried, and 5,820 g. of this substance is set aside for addition to a first herbal mixture.

Next 10 kg. of *Rhizoma Drynariae* are then heated, as by frying, with 1.5 kg. of crushed cane sugar until the herb takes on a brownish color. Sugar is used as the heating medium in order to reduce the bitter taste of the herb, thus improving palatability. It should be apparent that other flavorings or processing steps could instead be employed. 3,960 g. of this herb are then removed from the sugar and set aside for addition to the first herbal mixture.

The following herbs, after cleaning and drying, are measured out for addition to the first herbal mixture: 2,150 g. of *Herba Ecliptae*; 1,970 g. of *Radix Sophorae Flavescentis*; and 480 g. of *Pericarpium Trichosanthis.*

A small quantity of Chinese white vinegar is rubbed onto the surface of approximately 10 kg. of *Spina Gleditsiae.* Approximately 250 g. of Chinese rice wine is then sprayed onto the surface of the thusly prepared *Spina Gleditsiae.* This treated *Spina Gleditsiae* is then placed in an airtight container, such as a plastic or metal container, for a period of 48 hours, followed by removal and air drying. From this treated *Spina Gleditsiae* is removed 2,060 g. for addition to the first herbal mixture.

The thusly prepared and measured *Radix Polygoni Multiflori, Rhizoma Drynariae, Herba Ecliptae, Radix Sophorae Flavescentis, Spina Gleditsiae, Pericarpium Trichosanthis,* and *Radix Angelicae Sinensis* are added together and ground together to a powder form, yielding 16.94 kg. of this first herbal mixture.

A second herbal mixture is then prepared as follows. To 4,000 g. of water is added 1.5 kg. of crushed yellow cane sugar, which is dissolved to yield a sugar solution. To this solution is added 5 kg. of *Rhizoma Ligustici Chuanxiong,* which is allowed to seep for 72 hours, followed by boiling of the mixture for 4 hours. The thusly treated *Rhizoma Ligustici Chuanxiong* is then removed from the sugar solution and air-dried. From this, 1600 g. of treated *Rhizoma Ligustici Chuanxiong* is set aside for addition to the second herbal mixture.

Next, 2000 g. of *Spina Gleditsiae* that has been prepared with white vinegar and rice wine as for the first herbal mixture is heated until it has turned to a charcoal brown (not black) color. Traditionally, this heating is carried out by "frying" the herb in melted lead at a temperature of 350° C. While the use of lead is believed to increase the effectiveness of the composition, it does raise concerns about possible detrimental effect. It has been found that when prepared in this manner, lead is absorbed into the *Spina Gleditsiae* at a level of less than 1.40 parts per million, which is found to increase the hair darkening effect of the composition. It is not recommended that this composition be used by children or other individuals particularly susceptible to lead poisoning when the composition has been prepared in this manner. It should be readily apparent to those of skill in the an that alternate means of heating the herb could be utilized in place of melted lead, such as by heating in a convection oven. The heated herb is then peeled with a bristle brush. A measure of 950 g. of this treated herb is then set aside for addition to the second herbal mixture.

Next, 1000 g of clean and dry *Fructus Mori* is measured out for addition to the second herbal mixture. Additionally, 63.814 kg. (63,814 g.) of dry and clean *Indigo Naturalis* is ground into a fine powder form and set aside for addition to the second herbal mixture. Finally, 150 g. of *Calculus Bovis* is measured and ground into powder form.

The prepared *Rhizoma Ligustici Chuanxiong*, peeled *Spina Gleditsiae*, and *Fructus Mori* are added together and ground into powdered form, followed by mixing this powder with the powdered *Indigo Naturalis* and *Calculus Bovis*. This resulting second herbal mixture weighs 67.5 kg. Of this total second mixture, 1040 g. are set aside to add to the first herbal mixture.

The 16.9 kg. of the first mixture and the 1040 g. of the second herbal mixture are now added together and mixed to yield a compound that weighs 17.98 kg., which is then introduced to 45.0 kg. of water, followed by boiling for a period of not less than 90 minutes until a thick solution weighing between 18 and 20 kg. results. This solution is then distilled to form a compound solution weighing approximately 17 to 18 kg.

Next, 20 g. of Halitum (a crystal) are dissolved in from 20 to 30 g. of water by heating until the Halitum is dissolved. This solution is poured through a fine filter into the compounded solution of the first and second herbal mixtures. The resulting compounded solution of the first and second herbal mixtures and the dissolved Halitum is thoroughly mixed and yields the final herbal mixture that is ready for compounding with the oral retention base. This mixture is sufficient to yield approximately 2000 to 2400 tubes of toothpaste, each weighing approximately 64 g., or 300 sticks of chewing gum.

The composition of the chewing gum or toothpaste base is conventional and well-known to those of skill in the art of preparing such products. For example, a suitable toothpaste base includes calcium diphosphate, methyl cellulose, saccharine, glycerine, chlorophyll coloring, sodium lauryl sulfate, laurel flavoring and sodium pyrophosphate. Other toothpaste base formulations may be used, and may include a mild abrasive, such as sodium bicarbonate, flavoring agents such as sorbitol and mint, and sodium fluoride as is well-known for the prevention of tooth decay.

Gum bases are also well-known in the art, such as arabic, guar, or natural rubber gums, and sugar, saccharine, sorbitol, or other sweeteners and flavors such as mint.

In addition to a toothpaste or gum, other viscous media that can be readily retained within the mouth are suitable for use as a oral retention media for compounding with the herbal mixture. For example, a gel base such as an alginate and flavoring agents could be utilized.

The inventors additionally theorize that the present herbal mixture could be introduced to the bloodstream by direct absorption through the skin, such as by application with a transdermal patch.

The above described for preparing the herbal mixture of the present invention was developed using traditional Chinese herbalist techniques. It should be readily apparent to those of skill in the art that different production techniques may be developed through routine laboratory work.

Because these and other variations, substitutions, alterations, and modifications may be made by one of skill in the art based on the disclosure contained herein, it is intended that the scope of letters patent granted hereon be limited only by the definitions contained in the appended claims.

The invention claimed is:

1. An herbal-based oral composition for periodic retention within the oral cavity of a human, comprising:

a mixture of herbs included at a level of from 2.5 to 15% of the total composition weight, the mixture comprising *Radix Polygoni Multiflori, Rhizoma Drynariae, Rhizoma Ligustici Chuanxiong, Calculus Bovis, Indigo Naturalis, Herba Ecliptae, Pericarpium Trichosanthis, Radix Sophorae Flavescentis, Spina Gleditsiae, Radix Angelicae Sinensis,* and *Fructus Mori*, and Halitum; and an oral retention base selected from the group consisting of gels, pastes and gums.

2. A process for producing an herbal-based composition for promoting darkening of human hair color upon periodic retention of the composition within the mouth cavity, comprising compounding a mixture of herbs included at a level of from 2.5 to 15% of the total composition weight, the mixture comprising *Radix Polygoni Multiflori, Rhizoma Drynariae, Rhizoma Ligustici Chuanxiong, Calculus Bovis, Indigo Naturalis, Herba Ecliptae, Pericarpium Trichosanthis, Radix Sophorae Flavescentis, Spina Gleditsiae, Radix Angelicae Sinensis,* and *Fructus Mori*, and Halitum with an oral retention base selected from the group consisting of gels, pastes and gums.

3. A method of delivering an herbal product for promoting darkening of human hair color upon periodic retention of the composition within the oral cavity, comprising administering a mixture of herbs included at a level of from 2.5 to 15% of the total composition weight, the mixture comprising *Radix Polygoni Multiflori, Rhizoma Drynariae, Rhizoma Ligustici Chuanxiong, Calculus Bovis, Indigo Naturalis, Herba Ecliptae, Pericarpium Trichosanthis, Radix Sophorae Flavescentis, Spina Gleditsiae, Radix Angelicae Sinensis,* and *Fructus Mori*, and Halitum in an oral retention base selected from the group consisting of gels, pastes and gums to the oral cavity of a human for buccal absorption of extracts of the herbs.

* * * * *

UNITED STATES PATENT AND TRADEMARK OFFICE
CERTIFICATE OF CORRECTION

PATENT NO. : 5,466,443
DATED : November 14, 1995
INVENTOR(S) : S.K. Ho et al.

It is certified that error appears in the above-indentified patent and that said Letters Patent is hereby corrected as shown below:

| COLUMN | LINE | |
|--------|------|---|
| 2 | 53 | "grams" should read --64 grams-- |
| 3 | 13 | *"Angelicas"* should read --*Angelicae*-- |
| 4 | 59 | "an" should read --art-- |

Signed and Sealed this

Seventh Day of May, 1996

Attest:

BRUCE LEHMAN

Attesting Officer    Commissioner of Patents and Trademarks